United States Patent [19]

Spohn et al.

[11] Patent Number: 5,382,745
[45] Date of Patent: Jan. 17, 1995

[54] SEPARATING VINYLCYCLOHEXENE FROM A BUTADIENE EXTRACTING SOLVENT

[75] Inventors: Ronald F. Spohn, Getzville; Mohan S. Saran, Grand Island, both of N.Y.

[73] Assignee: Occidental Chemical Corporation, Niagara Falls, N.Y.

[21] Appl. No.: 235,738

[22] Filed: Apr. 29, 1994

[51] Int. Cl.$^6$ .............................................. C07C 7/00
[52] U.S. Cl. .................................. 585/800; 585/867
[58] Field of Search ............................. 585/800, 867

[56] References Cited

U.S. PATENT DOCUMENTS 4,292,141  9/1981  Lindner et al. .................. 203/49

FOREIGN PATENT DOCUMENTS 46-26741  4/1971  Japan .

Primary Examiner—Helen M. S. Sneed
Assistant Examiner—Nhat D. Phan
Attorney, Agent, or Firm—Wayne A. Jones; Richard D. Fuerle

[57] ABSTRACT

Disclosed is a method of separating a butadiene extracting solvent that forms an azeotrope with vinylcyclohexene from a mixture with vinylcyclohexene. The mixture is cooled to a temperature below 0° C. which results in the formation of a vinylcyclohexene phase over an extracting solvent phase and the two phases are physically separated. Also disclosed is apparatus suitable for performing this process.

17 Claims, 1 Drawing Sheet

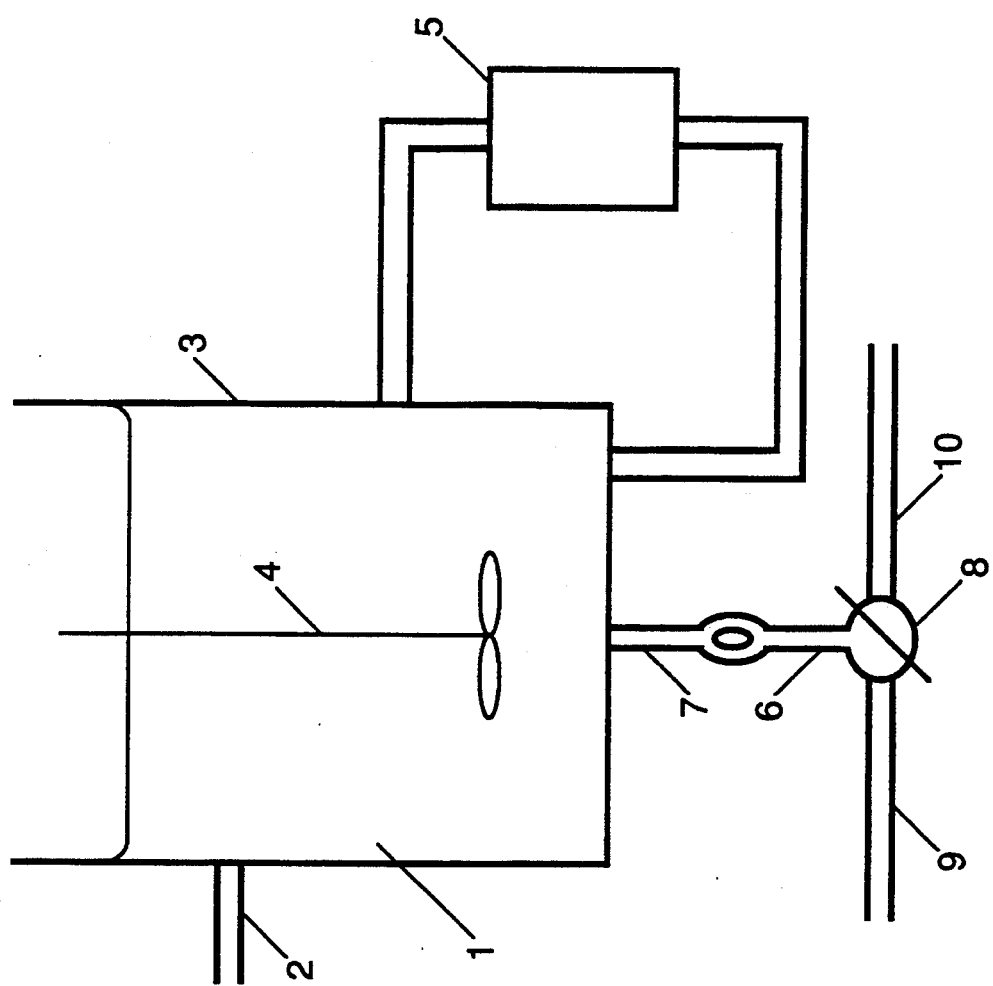

SEPARATING VINYLCYCLOHEXENE FROM A BUTADIENE EXTRACTING SOLVENT

BACKGROUND OF THE INVENTION

This invention relates to a method of separating vinylcyclohexene and a butadiene extracting solvent from a mixture thereof. In particular, it relates to cooling the mixture to a temperature below 0° C. which results in the formation of a vinylcyclohexene phase and an extracting solvent phase which are then physically separated.

In the manufacture of ethylene by cracking higher hydrocarbons, a sidestream of 4 carbon atom hydrocarbons is formed. This C$_4$ sidestream is about 45 wt % butadiene with the remainder being butanes, butenes, and butynes. After the butynes have been hydrogenated to butanes and butenes the gaseous mixture is bubbled into a column of extracting solvent, where the butadiene is extracted, thereby separating it from the other gases. The extracting solvent is then heated to drive off the butadiene which is purified by distillation.

Some of the butadiene in the extracting solvent dimerizes to form 4-vinylcyclohexene (VCH). VCH reduces the selectivity of extracting solvent for butadiene which results in the dissolution of more impurities into the extracting solvent. At the present time this problem is handled by continuously pulling out a 5 wt % slipstream of the extracting solvent after the butadiene has been removed. The slipstream is distilled to separate the VCH from the extracting solvent. The overhead from the distillation column is called "butadiene dimer oil" (BDO), a multi-component azeotrope which has a typical composition of about 50 wt % VCH, about 40 wt % extracting solvent and about 10 wt % hydrocarbon impurities. BDO can constitute a significant portion of the liquid waste of some ethylene manufacturing plants. There is at present no economical method of separating the VCH from the extracting solvent in the BDO. Since BDO has no utility for chemical processing it is simply burned as a fuel.

SUMMARY OF THE INVENTION

We have discovered that when BDO is cooled to a temperature at least as low as 0° C. it forms two phases, an upper phase of VCH and a lower phase of extracting solvent. While the extracting solvent in the lower phase contains some VCH, we have further discovered that the purity of the extracting solvent is a function of the temperature to which the BDO is cooled. That is, the lower the temperature to which the BDO is cooled, the fewer VCH and hydrocarbon impurities will enter the extracting solvent phase. As a result of this invention, it is now possible to recover extracting solvent of acceptable purity from BDO and recycle it for use in extracting more butadiene. The VCH recovered can be hydrogenated to make gasoline. Therefore, it is no longer necessary to use BDO as a waste fuel.

BRIEF DESCRIPTION OF THE DRAWING

The accompanying drawing is a diagram illustrating a certain presently preferred embodiment of an apparatus for performing the process of this invention.

In the drawing, BDO 1 from line 2 enters tank 3 which is fitted with a stirrer 4. BDO 1 in tank 3 is cooled by means of cooling unit 5. An exit conduit 6 fitted with a sight glass 7 is joined to a three-way valve 8 which permits fluid from conduit 6 to flow either through VCH conduit 9 or extracting solvent conduit 10.

The BDO used in the process of this invention typically comprises about 40 to about 60 wt % VCH, about 30 to about 50 wt % extracting solvent, and about 5 to about 15 wt % unidentified hydrocarbon impurities. The extracting solvent is an organic liquid that not only can extract butadiene, but which forms an azeotrope with VCH. (Extracting solvents such as dimethylformamide and N-methylpyrrolidone do not form an azeotrope with VCH and can be separated from VCH by distillation.) Examples of extracting solvents to which the method of this invention may be applicable include 2-furancarboxyaldehyde (known as "furfural"), 3-methoxypropionitrile (MOPN), 3-ethoxypropionitrile, and 4-methoxybutyronitrile. The preferred extracting solvents are 2-furancarboxyaldehyde (FUR) and MOPN as those are the extracting solvents that are used commercially. The commercial extracting solvent is a mixture of FUR and MOPN and can have the composition about 5 wt % to about 20 wt % FUR, about 70 to about 90 wt % MOPN and 5 to about 10 wt % water. The water is deliberately added to increase the selectivity of the extracting solvent for butadiene. If more than about 90 wt % MOPN is used, the butadiene may polymerize and the resulting polybutadiene may clog up the system. If more than about 20 wt % FUR is used, the amount of butadiene dissolved into the extracting solvent may decrease, and if more than about 10 wt % water is used, two phases may form.

We have further found that the addition of a nonpolar solvent to BDO may increase the purity of the VCH that is achieved at any particular temperature. Any straight-chain hydrocarbon can be used as a nonpolar diluent, including heptane or butane. However, some of the non-polar diluent enters the extracting solvent, which may reduce its selectivity for butadiene. Since it is generally more important to recover and recycle the extracting solvent, a non-polar diluent is preferably not used in the BDO. If a non-polar diluent is used, it is preferably used at about 20 to about 50 wt % (based on the total weight of BDO plus non-polar diluent) as less has little effect and more is unnecessary.

Cooling of the BDO to effect its separation into phases can be accomplished using dry ice, liquid nitrogen, or other coolant. The BDO must be cooled to a temperature of at least 0° C. in order for the two phases to begin to form and it is preferable to cool to at least −40° C. to achieve a practical separation of the phases. A preferred temperature range is about −60° to about −80° C. The VCH phase forms on top of the extracting solvent phase and the hydrocarbons that are in the BDO enter both phases.

The quantity of material in each layer depends upon the amount of hydrocarbon impurities in the BDO. The greater the amount of these impurities, the better the separation was. While this improved the completeness of the separating layers, it had only a minor effect on the quantity of MOPN and FUR recovered for recycle to the butadiene extraction process.

After the phases have formed, valve 8 in the drawing is opened to permit the extracting solvent to flow from tank 2 into extracting solvent conduit 10. The extracting solvent has a brownish color while the VCH is usually clear and almost colorless. An operator watches the fluid passing through conduit 6 by means of sight glass 7 and turns valve 8 so that the fluid enters VCH conduit 9 when it becomes colorless.

The following examples further illustrate this invention.

EXAMPLES

A vessel fitted with a cooling jacket and a bottom valve was filled to about ⅔ full with a BDO sample taken from a plant. The sample was cooled to −78° C. with stirring, which resulted in its separation into two layers. The viscosities of the two layers were determined at −78° C. using a Brookfield VLT viscometer. The lower layer viscosity was 200 to 250 cp (about the same viscosity of vegetable oil at room temperature) and the upper layer was ≦15 cp. The thicker, brown lower layer (45 wt % of total BDO) was removed through the bottom valve until the upper layer appeared. The upper layer (55 wt % of BDO) was then removed to a separate container. Both layers were warmed to ambient temperature. The BDO sample as received and both layers after cooling, separation, and warming were analyzed by gas chromatography (GC) Internal Standard (ISTD); and the following table gives the results.

| Component | BDO Sample | Upper Layer (Wt %) | Lower Layer (Wt %) |
| --- | --- | --- | --- |
| 4-vinylcyclohexene (VCH) | 44 | 68 | 19 |
| 3-methoxypropionitrile (MOPN) | 21.4 | 4.2 | 43 |
| 2-furfural (FUR) | 9.0 | 1.9 | 17 |
| 4-cyanocyclohexene or acrylonitrile-butadiene dimer | 4.9 | 2.4 | 9.3 |
| 2-furfurol | 0.03 | 0.01 | 0.03 |
| water | 1 | — | 2 |
| hydrocarbons | 19.67 | 23.5 | 10 |
| TOTALS | 100 | 100 | 100 |

The table shows that cooling of the crude BDO to −78° C. resulted in a 92% pure upper hydrocarbon layer and a lower layer which contained 91 wt % of the currently lost MOPN and FUR. When other samples were treated according to the method of this invention, 90 to 98 wt % of the currently lost MOPN and FUR was recovered.

We claim:

1. A method of separating a butadiene extracting solvent that forms an azeotrope with vinylcyclohexene from a mixture with vinylcyclohexene comprising cooling said mixture to a temperature below 0° C., whereby a vinylcyclohexene phase forms over an extracting solvent phase, and physically separating said phases.

2. A method according to claim 1 wherein said extracting solvent comprises about 5 to about 20 wt % 2-furan carboxyaldehyde, about 70 to about 90 wt % 3-methoxypropionitrile, and about 5 to about 10 wt % water.

3. A method according to claim 1 wherein said temperature is below −40° C.

4. A method according to claim 1 wherein said temperature is about −60° to about −80° C.

5. A method according to claim 1 wherein said cooling is achieved using dry ice.

6. A method according to claim 1 wherein said cooling is achieved using liquid nitrogen.

7. A method according to claim 1 wherein about 20 to about 50 wt % of a non-polar hydrocarbon diluent is added to said mixture.

8. A method according to claim 7 wherein said diluent is heptane.

9. A method according to claim 7 wherein said diluent is butane.

10. A method according to claim 1 wherein said mixture comprises about 40 to about 60 wt % vinylcyclohexene, about 30 to about 50 wt % extracting solvent, and about 5 to about 15 wt % hydrocarbon impurities.

11. A method of separating a mixture of about 40 to about 60 wt % vinylcyclohexene, about 30 to about 50 wt % extracting solvent, and about 5 to about 15 wt % hydrocarbon impurities into vinylcyclohexene phase and an extracting solvent phase where said extracting solvent comprises about 5 to about 20 wt % 2-furan carboxyaldehyde, 10 to about 90 wt % 3-methoxypropionitrile, and 5 to about 10 wt % water, comprising cooling said mixture to a temperature below about −40° C.

12. A method according to claim 11 wherein said temperature is about −60° to about −80° C.

13. A method according to claim 11 wherein said cooling is achieved using dry ice.

14. A method according to claim 11 wherein said cooling is achieved using liquid nitrogen.

15. A method according to claim 11 wherein about 20 to about 50 wt % of a non-polar hydrocarbon diluent is added to said mixture.

16. A method according to claim 11 wherein said diluent is heptane.

17. A method according to claim 11 wherein said diluent is butane.

* * * * *